United States Patent
Wagner

(10) Patent No.: US 10,287,674 B2
(45) Date of Patent: May 14, 2019

(54) COATING FOR A MEDICAL, DENTAL OR SURGICAL INSTRUMENT

(71) Applicant: W & H Dentalwerk Bürmoos GmbH, Bürmoos (AT)

(72) Inventor: Beate Wagner, Neunkirchen (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 336 days.

(21) Appl. No.: 15/018,276

(22) Filed: Feb. 8, 2016

(65) Prior Publication Data

US 2016/0168695 A1    Jun. 16, 2016

Related U.S. Application Data

(63) Continuation of application No. 13/762,233, filed on Feb. 7, 2013, now abandoned.

(30) Foreign Application Priority Data

Feb. 10, 2012    (EM) .................................... 12154820

(51) Int. Cl.
| | | |
|---|---|---|
| *C23C 16/40* | (2006.01) | |
| *A61C 1/08* | (2006.01) | |
| *A61B 17/00* | (2006.01) | |
| *A61C 19/00* | (2006.01) | |
| *C23C 16/02* | (2006.01) | |

(Continued)

(52) U.S. Cl.
CPC ............ *C23C 16/401* (2013.01); *A61B 17/00* (2013.01); *A61C 1/08* (2013.01); *A61C 19/00* (2013.01); *C23C 16/0281* (2013.01); *C23C 16/52* (2013.01); *A61B 2017/0088* (2013.01); *A61B 2017/00429* (2013.01); *A61B 2017/00526* (2013.01); *A61C 1/16* (2013.01); *Y10T 428/24364* (2015.01)

(58) Field of Classification Search
CPC ...................................................... C23C 16/22
USPC ................................... 428/698; 427/255.394
See application file for complete search history.

(56) References Cited

U.S. PATENT DOCUMENTS

| | | |
|---|---|---|
| 5,527,340 A | 6/1996 | Vogel |
| 6,406,475 B1 | 6/2002 | Wenzler et al. |

(Continued)

FOREIGN PATENT DOCUMENTS

| | | |
|---|---|---|
| DE | 19828976 | 2/2000 |
| EP | 0517244 | 12/1992 |

(Continued)

OTHER PUBLICATIONS

Ninomiya et al., "New Application of Low Expansion Glass-Ceramics," *New Glass* 20(3):22-28, 2005.

(Continued)

*Primary Examiner* — Andrew J Bowman
(74) *Attorney, Agent, or Firm* — Klarquist Sparkman, LLP

(57) ABSTRACT

A medical, dental or surgical instrument comprising a substrate on at least part of the instrument with a rough surface structure and a layer which is applied to or deposited on the substrate in such a way that the rough surface structure of the substrate is at least not completely smoothed by the layer or the roughness is increased, wherein the layer applied to or deposited on the substrate is embodied as a glass-ceramic layer. In addition, for producing such an instrument or part thereof is described.

20 Claims, 2 Drawing Sheets

(51) Int. Cl.
   *C23C 16/52* (2006.01)
   *A61C 1/16* (2006.01)

(56) References Cited

U.S. PATENT DOCUMENTS

| | | |
|---|---|---|
| 6,737,120 B1 | 5/2004 | Golecki |
| 2004/0091750 A1* | 5/2004 | Oliver ............ A61C 1/16 428/698 |
| 2004/0121893 A1* | 6/2004 | Minamikawa ...... C03C 10/0045 501/4 |
| 2004/0224786 A1 | 11/2004 | Reardon et al. |
| 2007/0172661 A1 | 7/2007 | Fechner et al. |
| 2007/0287123 A1 | 12/2007 | Swift et al. |
| 2009/0042710 A1 | 2/2009 | Minamikawa |
| 2010/0173167 A1 | 7/2010 | Vissing et al. |
| 2011/0217470 A1 | 9/2011 | Kasanovic et al. |
| 2011/0293923 A1* | 12/2011 | Schmidt ............ C23C 18/1208 428/329 |

FOREIGN PATENT DOCUMENTS

| | | |
|---|---|---|
| JP | 2001019574 | 1/2001 |
| JP | 2003506295 | 2/2003 |
| JP | 2004-524118 | 7/2004 |
| JP | 2004524118 | 8/2004 |
| JP | 2007-504052 | 3/2007 |
| JP | 20112419092 | 12/2011 |
| WO | WO 2005/026069 | 3/2005 |

OTHER PUBLICATIONS

International Search Report dated Jun. 15, 2012 from related European Patent Application No. EP12154820.
Office Action dated Jan. 7, 2014 from related Canadian Patent Application No. 2,802,474.
Office Action dated Jan. 21, 2014 from related Japanese Patent Application No. 2013-017835.
Office Action dated Aug. 18, 2014 from related Japanese Patent Application No. 2013-017835.

* cited by examiner

COATING FOR A MEDICAL, DENTAL OR SURGICAL INSTRUMENT

CROSS REFERENCE TO RELATED APPLICATION

The present application is a continuation of U.S. patent application Ser. No. 13/762,233, filed Feb. 7, 2013, which claims priority from pending European Patent Application No. 12154820.0, filed Feb. 10, 2012, which is incorporated herein by reference.

BACKGROUND

Field

This application relates a medical, dental or surgical instrument with a layer applied to or deposited over at least a part thereof and a method for producing a medical, dental or surgical instrument having such a layer.

Description of Prior Art

US Patent Application US 2004/0091750 A1 discloses a medical instrument whose surface is coated with a plastic, in particular Teflon for repelling dirt. The plastic layer is of such a type that the roughness of the surface is preserved so that a user can hold the medical instrument securely. Thus two desired, often mutually exclusive properties of a surface of a medical instrument are to be implemented by this Teflon coating, namely repelling dirt from the surface and a secure hold on the instrument by the user.

One disadvantage of a medical instrument whose surface is provided with a plastic layer, in particular a Teflon layer consists of the fact that the plastic layer or the Teflon layer is very sensitive to mechanical effects. In practice this means that the plastic or Teflon layer of the medical instrument is damaged after just a short period of time, for example, due to abrasion or due to contact with other instruments and their efficacy is reduced or lost.

It would be desirable to create a surface of a medical instrument, in particular a dental or surgical instrument or instrument part or a coating for a surface of a medical instrument, in particular a dental or surgical instrument or instrument part, which is less sensitive to mechanical influences while retaining the two desired properties mentioned above, i.e., repelling dirt from the surface and allowing the user to achieve a secure, tight hold on the instrument.

SUMMARY

Described below is a medical, dental or surgical instrument that addresses the short comings of the prior art. The medical, dental or surgical instrument comprises a substrate on at least part of the instrument having a rough surface structure and a layer which is applied to the substrate or deposited thereon in such a way that the rough surface structure of the substrate is not completely smoothed by the layer or the roughness is increased, wherein the layer applied to or deposited on the substrate is designed as a glass-ceramic layer.

The glass-ceramic layer or glass-ceramic substance is preferably understood to be a mixture or a composite material of amorphous glass or an amorphous glass-like matrix and polymerized, preferably organic, components contained therein. The glass-ceramic layer or glass-ceramic substance preferably has an amorphous layer structure. According to one embodiment, the glass-ceramic layer applied to or deposited on the substrate contains silicon, in particular silicon oxide and/or at least one (plasma) polymerized silicon compound, preferably one that is at least partially organic. According to another embodiment, the glass-ceramic layer or glass-ceramic substance comprises a mixed structure of silicon dioxide and/or amorphous quartz-like layers with organic plasma-polymerized components incorporated into them.

The use of a glass-ceramic substance or layer for coating a surface of a medical instrument, in particular a dental or surgical instrument or instrument part has the following advantages:

Preferably the glass-ceramic layer is applied to or deposited on the substrate in such a thin layer that the roughness of the substrate is at least not completely smoothed out, but preferably is essentially preserved or is even slightly increased. Preferably the glass-ceramic layer follows or corresponds essentially to the surface structure of the substrate, in particular without smoothing out recesses or substantially or completely filling them out. The layer thickness of the glass-ceramic layer applied to or deposited on the substrate is preferably approximately 1 to approximately 8 µm, in particular about 3 to about 8 µm on exterior parts of instruments, for example, an outer sleeve, and about 1 to about 5 µm on the internal parts of instruments, for example, a tool holding device or a shaft. The roughness of the substrate, which is thus essentially preserved, and/or the resulting or developed roughness of the layer applied to or deposited on the substrate makes it possible for the user to hold the instrument or instrument part securely and with as little slippage possible.

The roughness of the substrate to which the glass-ceramic layer has been applied to or deposited preferably amounts to approximately Ra=about 0.5 to about 1.5 µm and/or Rz=about 3 to about 12 µm. The roughness of the glass-ceramic layer deposited on or applied to the substrate is preferably approximately Ra=about 0.5 to about 1.8 µm and/or Rz=about 3 to about 14 µm.

The glass-ceramic layer is preferably applied to or deposited on the substrate such that it is preferably essentially closed or pore-free and thus has a dirt-repellent property and a high barrier property, in particular with respect to gas and water vapor diffusion. The glass-ceramic layer, in particular the surface of the glass-ceramic layer, is preferably modified so that the glass-ceramic layer, in particular its surface, receives hydrophobic surface properties. The modification is made, for example, by adjusting or controlling the oxygen content during the coating process (see below). The hydrophobic surface property additionally increases the dirt-repellent properties of the glass-ceramic layer. If desired, it is also possible to modify the glass-ceramic layer, in particular its surface, so that it has hydrophilic surface properties.

Finally, the glass-ceramic layer is mechanically much stronger in comparison with the Teflon coating known from the prior art and is thus much more resistant to abrasion and contact with sharp edges or cutting edges, for example, other medical instruments. The hardness or mechanical strength of the glass-ceramic layer is about 600 to about 800 HV, preferably approximately 700 HV, for example.

Another advantage of the glass-ceramic layer is that it is preferably essentially chemically inert. The glass-ceramic layer is thus essentially also corrosion-resistant, in particular resistant to corrosive cleaning media and water vapor.

In addition, the glass-ceramic layer is preferably designed so that it withstands temperature changes of approximately 100° C.-200° C. so that preferably it can be exposed with no problem to known cleaning or sterilization processes having such temperature changes, in particular at least several hundred times. The glass-ceramic layer in particular has a very low thermal expansion coefficient in different temperature ranges so that breakage due to thermal shock is thereby prevented. The thermal expansion coefficient is at least $0.55 \cdot 10^{-6} K^{-1}$, for example.

According to one embodiment, the applied or deposited glass-ceramic layer is transparent. It is thus possible in an advantageous manner to shape geometric and/or alphanumeric structures or shapes, for example, edges, knurls, characters, numerals, trademarks, logos, instructions for use or warnings on the instrument or on the instrument part so that these structures or shapes are discernible or visible for the user due to the transparency of the glass-ceramic layer.

It is advantageously possible to apply or deposit the glass-ceramic layer optionally on a substrate formed by a metal, in particular a substrate of steel or brass or on a substrate formed by a plastic. According to one embodiment an intermediate layer or an adhesion promoting layer, for example, a metal alloy, preferably a nickel-chromium layer is provided between the substrate or the surface of the instrument or the instrument part and the glass-ceramic layer. According to one alternative embodiment the glass-ceramic layer is applied or deposited directly (i.e., without an adhesion promoting layer or intermediate layer) on the substrate or the surface of the instrument or the instrument part.

The glass-ceramic layer is preferably deposited or applied on the substrate or the surface by a CVD (chemical vapor-deposition) method forming a plasma. In this plasma-supported CVD method, which is known per se, the gas and/or the components contained in the gas which are to be deposited are converted to the plasma state with the help of a high-frequency voltage. The gas or the components to be deposited are in a very high energy level in the plasma state and then are deposited on the substrate or the surface. It is possible to achieve the deposition of a glass-ceramic layer through a suitable choice of process parameters of the method, for example, the magnitude or duration of the energy input to form the plasma, the gas pressure or the oxygen content in the plasma gas.

The gas contains in particular organosilicon compounds or silane gas and the oxygen content in the plasma gas is selected so that the oxygen is not sufficient to convert the organosilicon compounds or silane gas (completely) to silicon dioxide, carbon dioxide and water, thus forming the glass-ceramic layer in particular with its amorphous quartz-like structure with incorporated organic plasma-polymerized components. Thus preferably at least the quantitatively excessive formation of crystals in particular of silicon dioxide is prevented by the plasma-supported CVD process, in particular due to the (low or substoichiometric) oxygen concentration and the formation or deposition of a glass-ceramic layer which is closed in particular or is continuous is made possible only in this way.

An instrument or an instrument part which is provided with the glass-ceramic layer may be embodied, for example, as a handheld element, a handle, a handpiece, a contra-angle handpiece, an adaptor, a drive unit, a coupling device, an air motor or electric motor or as a part thereof. The instrument or instrument part may of course have various shapes, for example, straight, curved, angled or pistol shaped and it may be in one or more parts and may also be designed to dispense and/or receive and/or relay mechanical and/or electrical energy and/or at least one fluid. According to a preferred embodiment, the medical instrument, in particular the dental or surgical instrument or instrument part which is provided with the glass-ceramic layer comprises a media-dispensing device for dispensing a medium in the direction of a treatment site, in particular for dispensing a fluid and/or electromagnetic energy and/or a tool mount for a tool that acts on a treatment site and can be set in motion by an (electrical or fluid-operated) drive device. According to another preferred embodiment, the instrument or instrument part which is provided with the glass-ceramic layer is designed as an active mechanical instrument or instrument part, i.e., as a medical instrument or instrument part, the operation of which must rely at least partially on an electrical energy source or on any energy source other than the energy generated directly by the human body or by the force of gravity, for example, on an energy source which provides fluid, in particular compressed air.

According to the invention, the surface or substrate having a glass-ceramic layer comprises not only surfaces or substrates on the outside, on the outer shell or on the outside circumference of a medical instrument or instrument part, but of may course also include surfaces or substrates in the interior of such an instrument or instrument part or surfaces or substrates on coupling faces, joining faces, interfaces or contact faces of a medical instrument or instrument part. Components with a glass-ceramic layer arranged in the interior of a medical instrument or instrument part may comprise, for example, at least parts of a shaft, a tool-holding device, a bearing or a media line or a fluid line, which should be dirt-repellent or corrosion-resistant in particular.

A method for producing a medical instrument, in particular a dental or surgical instrument or instrument part, preferably an active medical, in particular dental or surgical instrument or instrument part is defined in that a glass-ceramic layer is applied to or deposited on at least one component of the instrument or instrument part which has a substrate with a rough surface structure so that the rough surface structure of the substrate is at least not completely smoothed by the glass-ceramic layer so that the rough surface structure of the substrate develops at least partially into the applied or deposited glass-ceramic layer or the roughness of the surface structure is increased.

The glass-ceramic layer deposited on or applied to the substrate by the production method defined above preferably contains silicon, in particular silicon oxide and/or at least a (plasma-)polymerized, preferably at least partially organic silicon compound.

The glass-ceramic layer applied to or deposited on the substrate by the production process defined above is preferably transparent and/or has a hydrophobic surface property. Particularly before or after applying or depositing the transparent glass-ceramic layer on the substrate an alphanumeric structure or shape, for example, a character, a numeral, a trademark, a logo, an instruction for use or a warning is formed on the instrument or on the instrument part or on the substrate.

The glass-ceramic layer applied to or deposited on the substrate is preferably deposited on the surface or on the substrate by a CVD (chemical vapor-deposition) process forming a plasma.

Following is a description of embodiments with reference to the accompanying drawings:

DETAILED DESCRIPTION

Figure 1:
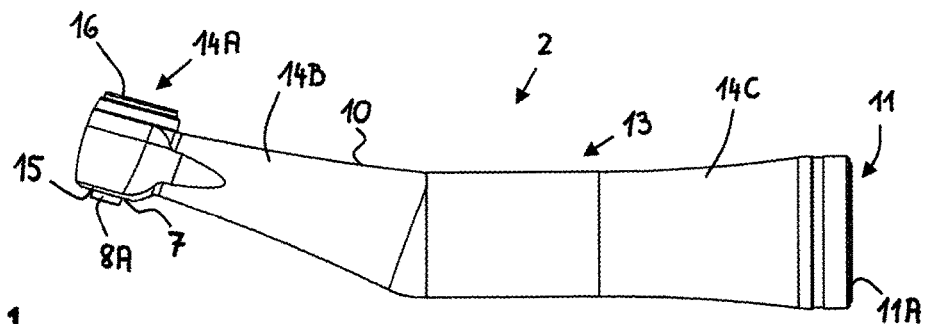
FIGS. 1-4 show four embodiments of medical instruments, in particular dental or surgical instruments or instrument parts having at least one surface with a glass ceramic layer.
Figure 2:
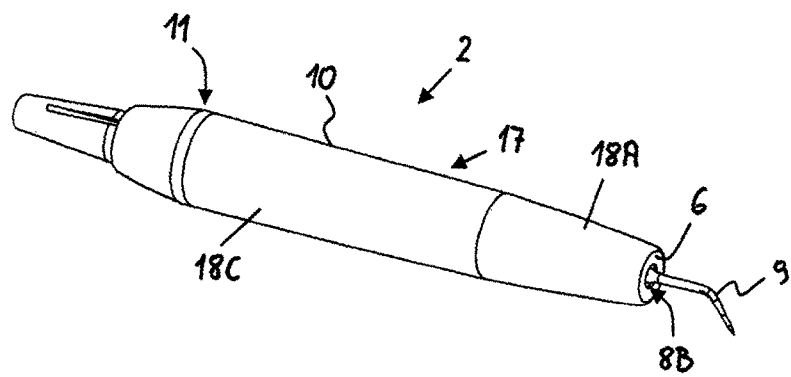

FIG. 1 shows a first embodiment of a medical, dental or surgical instrument 2 (or part thereof) in the form of a handle element, in particular a curved or contra-angled handpiece 13. FIG. 2 shows a second embodiment of an instrument in the form of a handle element, in particular a straight handpiece 17, preferably for removing dental calculus. Due to their great number of identical or similar components the two handle elements 13, 17 will be described jointly in the following.

The instruments 2 comprise a head part 14A, 18A, preferably a neck part 14B connected to the former and a main part 14C, 18C connected thereto. The main part 14C of the angle piece 13 is arranged at an angle to the neckpiece 14B, whereas the two parts 18A, 18C of the handpiece 17 are arranged in a straight line, i.e., essentially along a shared central axis. The parts 14A-14C and 18A, 18C have a one-piece or multi-piece outer shell 10.

A tool mount or tool holding device 8A, 8B, preferably detachable, for receiving or holding a treatment tool 9 is provided in or on the head part 14A, 18A. The tool mount 8A, 8B and the treatment tool 9 can preferably be induced to an operating motion, for example, a rotational motion, a lifting motion, a reciprocating motion or a vibrating motion. The tool mount 8A, 8B is designed as a friction-locking or positive connecting device or as a screw connection, for example.

A first media-dispensing device 7 for dispensing at least one medium, in particular air and/or water is preferably provided on the head part 14A, 18A of the instrument 2, in particular adjacent the tool mount 8A, 8B or around the tool mount 8A, 8B and/or around a tool receptacle 15 of the outer sleeve 10, alternatively on the neck part 14B. The first media-dispensing device 7 comprises, for example, one or more lines, openings and/or nozzles from which a medium can be dispensed in the direction of the treatment site and/or the tool or an opening for connection to a fluid bore in the tool 9.

A media dispensing device in the form of a light-dispensing device 6 for dispensing light in the direction of the treatment site, for example, an optical fiber and/or a light source, preferably a light-emitting diode LED is provided on the head part 14A, 18A, in particular around the tool mount 8A, 8B and/or the tool receptacle opening 15 of the outer sleeve 10, alternatively on the neck part 14B.

The instruments 2, in particular the contra-angle handpiece 13, preferably additionally comprise a tool release device for releasing the tool out of the tool mount 8A. The tool-releasing device is operable, for example, by means of an operating element 16 which is accessible from the outside for the user, in particular by means of a pushbutton or a key. The operating element 16 is preferably provided on the head part 14A, preferably substantially opposite the tool receptacle opening 15.

The tool mount 8A, 8B and the treatment tool 9 can optionally be set in motion by means of a drive device provided in the instruments 2 or by means of a separate drive unit which is detachable from the instruments 2. The drive device provided in the instruments 2 comprises, for example, a rotary part that can be driven by a fluid, in particular by compressed air, in particular a turbine, a flywheel or a rotary sleeve rotatably arranged in the head part 14A or an electrically operable drive device, for example, an electric motor or a piezoelectric drive or a magnetostrictive drive. The separate drive unit that can be detached from the instruments 2 comprises, for example, a motor unit, e.g., an electric motor or a vane motor or an air motor (see FIG. 3).

A connecting or coupling device 11 is provided on the main part 14C, 18C for detachable connection or coupling of the instruments 2 to the releasable separate drive unit and/or to a control or regulating unit. The connecting device 11 comprises a contact face 11A which contacts a mating contact face of the releasable separate drive unit when the instruments 2 are connected to the drive unit and/or of a control or regulating unit and is exposed when the instruments 2 are separated from the drive unit and/or from the control or regulating unit. The connecting device 11 is designed, for example, as a plug connection, screw connection, bayonet connection or as a rotary coupling. The connecting device 11 is preferably designed for transmitting at least one medium and/or data, for example, for conveying a fluid, in particular water or air, electromagnetic radiation, electricity and/or electrical signals. To do so one or more electric lines, fluid lines, electric contacts, optical conductors and/or electric, optical or fluid connecting elements are provided on the connecting device 11 and of course also similarly on the releasable separate drive unit and/or control unit or regulating unit.

Components for transferring a drive motion and/or for conducting a medium and/or data and/or electrical signals are preferably provided in the neck part 14B and/or in the main part 14C, 18C, for example, one or more shafts that can be set in motion, a vibrating shaft, a gear, one or more lines or channels for a fluid, an optical fiber or electrical lines for the transmission of electrical signals or data.

Figure 3:
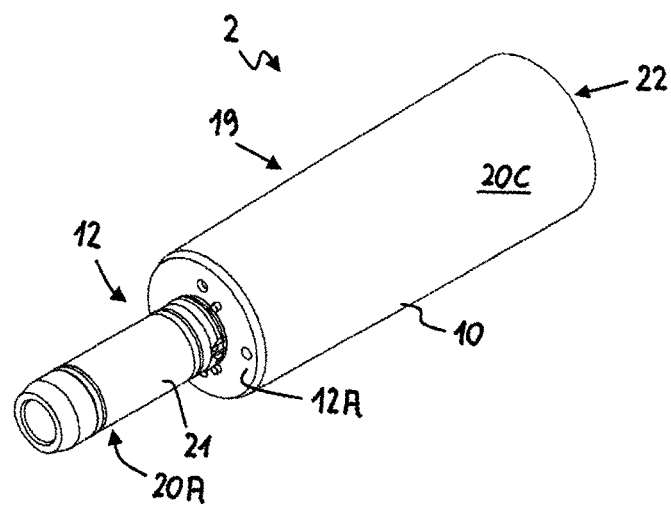
Figure 4:
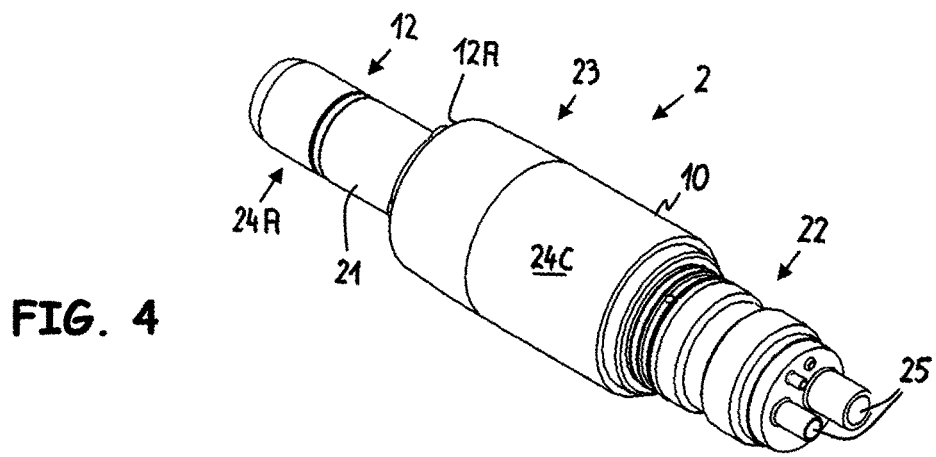

FIG. 3 shows a medical instrument, in particular a dental or surgical instrument or instrument part 2 in the form of a drive unit 19 for generating a drive motion. The drive unit 19 is embodied in particular as a motor unit, preferably as an electric motor or a vane motor or an air motor. FIG. 4 shows a medical instrument, in particular a dental or surgical instrument or instrument part 2 in the form of an adaptor or a coupling 23. Because of the numerous similar or identical components, the two instruments 2, i.e., the drive unit 19 and the coupling 23 are described jointly below.

The two instruments 2 each include a one-part or multi-part outer sleeve 10. The instruments 2 and/or their outer sleeves 10 have a main part 20C, 24C and a connecting part 20A, 24A, preferably in the form of a coupling device 12, which is connected to the main part 20C, 24C. The instruments 2 can be connected to a tool by means of the connecting part 20A, 24A so that the drive motion generated by the drive unit 19 and/or at least one medium, in particular a fluid and/or electromagnetic radiation can be transferred to the tool. The connecting part 20A, 24A is designed, for example, as a plug connection, a screw connection, a bayonet connection or a rotary coupling.

The coupling device 12 comprises, for example, a coupling pipe or a coupling journal 21 and a contact or coupling face 12A. The coupling face 12A is designed to contact a mating contact face of an instrument that can be detachably connected to the drive unit 19 or the coupling/adaptor 23, for example, the mating contact face 11A of the handpiece 13 when the drive unit 19 or the coupling/the adaptor 23 is connected to the instrument. The coupling face 12A is exposed when the instrument is detached from the drive unit 19 or the coupling/adaptor 23.

The motor or at least a large portion of the motor components is arranged in the main part 20C of the drive unit 19, for example, the rotor, the stator, a control or regulating element for the motor, electric or fluid supply lines for driving and/or cooling the motor, one or more sensors for monitoring the operation of the motor, a rotor shaft, etc. According to a preferred embodiment, an electrodynamic converter (generator) may be arranged in the main part 24C of the coupling/adaptor 23 and may supply electrical energy for supplying an electrical load in the coupling/adaptor 23 and/or in an instrument connectable thereto, for example, the handpiece 13.

According to one embodiment, a shaft, for example, at least a part of the rotor shaft or a shaft connected to the rotor shaft and/or an entraining element for transferring or relaying a drive motion, in particular the drive motion generated by the drive unit 19 is arranged in the coupling journal 21, in particular in the coupling journal 21 of the drive unit 19.

On the end of the instruments 2 opposite the coupling device 12 or on the respective free end of the main part 20C, 24C, a connecting device 22, preferably detachable, for connection of the instruments 2 to a supply and/or control or regulating unit is provided. The supply and/or control or regulating unit supplies the drive unit 19, in particular its motor or the coupling/adaptor 23, in particular its generator with a drive medium, for example, and/or a cooling medium and/or electrical signals and/or it preferably receives at least one electrical signal or data from the drive unit 19 or the coupling/adaptor 23. The connecting device 22 accordingly preferably comprises one or more media transfer elements, for example, electric lines for power supply and/or for data exchange, fluid lines 25, optical conductors, electric contacts and/or electric, optical or fluid connecting elements.

The drive unit 19 and the coupling/adaptor 23 are therefore preferably designed to transmit at least one medium, for example, a fluid, in particular water or compressed air, electrical energy, an electric signal or electromagnetic radiation, in particular light to a tool or instrument connected or connectable to the drive unit 19 or the coupling/adaptor 23, for example, a handpiece 13 or from a tool or instrument, for example, a handpiece 13 which is or can be connected to the drive unit 19 or to the coupling/adaptor 23. To do so one or more media transfer elements are preferably provided, for example, electric lines, fluid lines, optical conductors, electric contacts and/or electric, optical or fluid connecting elements are preferably provided on the connecting part 20A, 24A, in particular on the coupling face 12A and/or on the coupling journal 21. For supplying the media transfer elements of the connecting part 20A, 24A, they are connected to the media transfer elements of the connecting device 22 via the drive unit 19 or the coupling/adaptor 23 via electrical, optical and/or fluid lines passing through the drive unit 19 or the coupling/adaptor 23.

Figure 5:
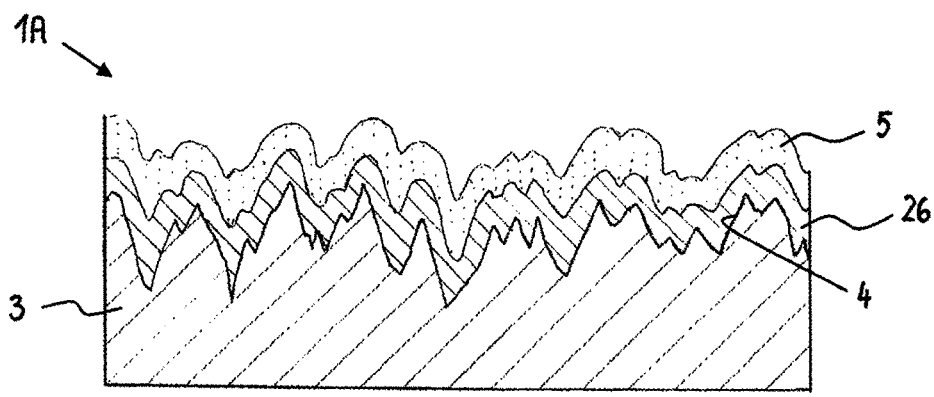
FIG. 5 shows a first embodiment of a glass-ceramic layer of a medical instrument, in particular a dental or surgical instrument or instrument part.
Figure 6:
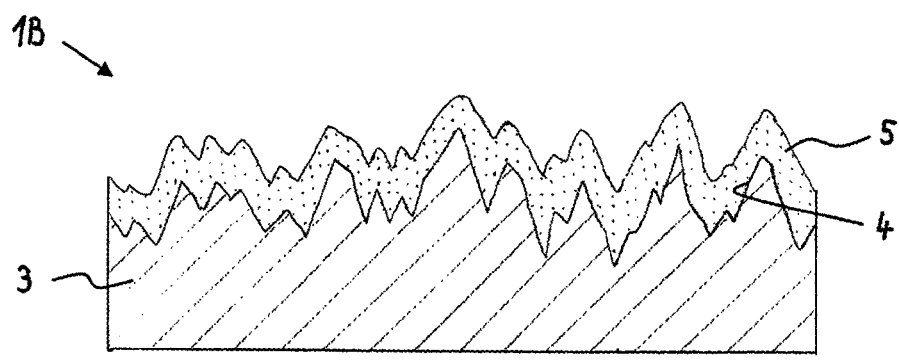
FIG. 6 shows a second embodiment of a glass-ceramic layer of a medical instrument, in particular a dental or surgical instrument or instrument part.

At least one component or one surface 1A, 1B of a component of the instruments 2, 13, 17, 19, 23 described above from FIGS. 1-4 is provided with a glass-ceramic layer 5, for example, at least a part of the outer sleeve 10 and/or of the connection device 11, in particular its contact face 11A and/or of the coupling device 12, in particular its contact face 12A and/or of the operating element 16 and/or of the tool mount or tool holding device 8A, 8B is/are provided with the layer. FIGS. 5 and 6 show two embodiments of such a glass-ceramic layer 5 which may optionally be applied to or deposited on a surface 1A, 1B of at least one component of the instruments 2, 13, 17, 19, 23 of FIGS. 1-4 as described above.

The surface 1A according to FIG. 5 comprises a substrate, for example, a metal or a plastic. The substrate is formed, for example, by the outer sleeve 10 or its outermost layer. However the substrate may of course also comprise any other component of the instrument 2. The substrate 3 has a rough surface or surface structure 4 which is represented in FIG. 5 by the zigzag pattern of the surface of the substrate 3 resembling mountains and valleys. An intermediate layer or an adhesion-promoting layer 26 is provided on the substrate 3. The intermediate layer 26 according to one embodiment comprises a metallic layer, for example, a metal alloy, in particular a nickel chromium layer. The intermediate layer 26 preferably has a thickness of approximately about 2 µm to about 5 µm.

The glass-ceramic layer 5 is arranged on the intermediate layer 26. As FIG. 5 shows, the glass-ceramic layer 5 just like the intermediate layer 26 essentially follows the rough surface or surface structure 4 of the substrate 3. The rough surface structure 4 of the substrate 3 is thus at least not completely smoothed by the glass-ceramic layer 5, so that a secure hold with the least slippage possible of the instrument or instrument part 2 and with the most secure possible hold for the user is provided. FIG. 5 also shows that the glass-ceramic layer 5 is applied to or deposited on the substrate 3 or the intermediate layer 6 in an essentially homogeneous or uniform manner, so there is a dense uniform pore-free surface coating which is thus also dirt-repellent. The glass-ceramic layer 5, for example, has a thickness of approximately 1 µm to approximately 8 µm, preferably a thickness of approximately about 3.5 µm to about 6 µm, in particular a thickness of approximately 4 µm. As already explained in detail above, the glass-ceramic layer 5 comprises a mixture of amorphous glass or of an amorphous glass-like matrix and (plasma) polymerized, preferably organic components contained therein In particular the glass-ceramic layer 5 contains silicon, in particular silicon oxide/silicon dioxide and/or at least one (plasma-)polymerized, preferably at least partially organic silicon compound.

The surface 1B shown in FIG. 6 corresponds in its structure and properties essentially to the surface 1A of FIG. 5, so that reference is made to the description in this regard to avoid repetition. However, in contrast with the surface 1A, the surface 1B does not have an intermediate layer 26. Thus the glass-ceramic layer 5 is arranged directly on the substrate 3, i.e., for example, on the outer sleeve 10 of the instrument 2. Direct application or deposition of the glass-ceramic layer 5 without the intermediate layer is possible with a metallic substrate as well as with a substrate made of plastic.

This disclosure is not limited to the embodiments described here but instead includes all the embodiments that apply or comprise the appropriate function principle. In addition, all features of all embodiments that have been described and presented can be combined with one another.

What is claimed is:

1. A method for depositing a layer on at least a portion of a medical, dental or surgical instrument, comprising:
providing a medical, dental or surgical instrument comprising a portion having a first surface having a first roughness; and
depositing a layer on the portion by a chemical vapor-deposition process to produce an amorphous glass-ceramic layer on the first surface, the glass-ceramic layer having a hydrophobic second surface and a hardness value of 600 HV to 800 HV, the hydrophobic second surface also having a second roughness that is substantially the same as the first roughness, greater than the first roughness, or less than the first roughness but not completely smooth, the second roughness facilitating a secure hold by a user on the instrument portion comprising the layer, the chemical vapor-deposition process comprising using an organosilicon compound, silane gas, or a combination thereof, selecting an oxygen concentration to produce the amorphous glass-ceramic layer, and adjusting the oxygen concentration to produce the hydrophobic second surface.

2. The method of claim 1, wherein the first roughness is approximately Ra=about 0.5 to about 1.5 µm and/or Rz=about 3 to about 12 µm.

3. The method of claim 1, wherein the second roughness is approximately Ra=about 0.5 to about 1.8 µm and/or Rz=about 3 to about 14 µm.

4. The method of claim 1 comprising depositing the layer to produce an amorphous glass-ceramic layer having a thickness of from 1 µm to 8 µm.

5. The method of claim 1, wherein the first surface comprises metal or plastic.

6. The method of claim 1, wherein the glass-ceramic layer comprises at least one polymerized silicon compound, at least one partially organic silicon compound, or a combination thereof.

7. The method of claim 1, wherein reactants used in the CVD process consist essentially of a silane gas, an organosilicon compound, combinations thereof, and oxygen.

8. The method of claim 1, wherein the medical, dental or surgical instrument comprises an adhesion-promoting layer comprising the first surface.

9. The method of claim 8, wherein the adhesion-promoting layer comprises a metal alloy layer.

10. The method of claim 1, wherein depositing the layer comprises depositing a transparent amorphous glass-ceramic layer.

11. A method for making a medical, dental or surgical instrument comprising an outer sleeve and a tool-releasing device having an operating element, the instrument comprising an amorphous glass-ceramic layer on at least a portion of the outer sleeve and the operating element, the method comprising:
providing the outer sleeve, the tool-releasing device and the operating element, the outer sleeve and the operating element comprising a metal alloy layer having a thickness of from about 2 µm to about 5 µm and a first surface having a first roughness of approximately Ra=about 0.5 to about 1.5 µm and/or Rz=about 3 to about 12 µm; and
forming the amorphous glass-ceramic layer on at least a portion of the outer sleeve and the operating element, the glass-ceramic layer comprising at least one polymerized silicon compound, at least one partially organic silicon compound, or a combination thereof, the glass-ceramic layer being formed by a chemical vapor-deposition process, the layer having a hardness value of 600 HV to 800 HV, a thickness of from 1 µm to 8 µm, and a hydrophobic second surface having a second roughness of from about 0.5 to about 1.8 µm Ra, and/or from about 3 to about 14 µm Rz, wherein the chemical vapor-deposition process comprises using an organosilicon compound, silane gas, or a combination thereof, selecting an oxygen concentration to produce the amorphous glass-ceramic layer, and adjusting the oxygen concentration to produce the hydrophobic second surface.

12. A method for making a medical, dental or surgical instrument having a layer deposited on a first surface of the medical, dental or surgical instrument, comprising depositing the layer on the medical, dental or surgical instrument by a chemical vapor-deposition process to produce an amorphous, glass-ceramic layer on the first surface, the glass-ceramic layer having a hydrophobic second surface and a hardness value of 600 HV to 800 HV, the hydrophobic second surface also having a second roughness, the second roughness facilitating a secure hold by a user on the instrument comprising the layer, the chemical vapor-deposition process comprising using an organosilicon compound, silane gas, or a combination thereof, selecting an oxygen concentration to produce the amorphous glass-ceramic layer, and adjusting the oxygen concentration to produce the hydrophobic second surface.

13. The method of claim 12, wherein the first roughness is approximately Ra=about 0.5 to about 1.5 µm and/or Rz=about 3 to about 12 µm.

14. The method part of claim 12, wherein the second roughness is approximately Ra=about 0.5 to about 1.8 µm and/or Rz=about 3 to about 15 µm.

15. The method of claim 12, wherein the glass-ceramic layer has a thickness of from 1 µm to 8 µm.

16. The method of claim 12, wherein the instrument comprises a metal alloy adhesion-promoting layer comprising the first surface.

17. The method of claim 12, wherein the amorphous, glass-ceramic layer is a transparent, amorphous glass-ceramic layer.

18. The method of claim 12, wherein the glass-ceramic layer comprises at least one polymerized silicon compound, at least one partially organic silicon compound, or a combination thereof.

19. The method of claim 12 wherein the instrument comprises at least one of an outer surface of a medical, dental or surgical instrument; a gripping surface of a medical, dental or surgical instrument; and/or a handle portion of a medical, dental or surgical instrument.

20. The method of claim 12, wherein the instrument further comprises a media dispensing device for dispensing a medium in the direction of a treatment site and a tool mount that can be set in motion by a drive device for a tool acting on a treatment site.

* * * * *